(12) United States Patent
Zhou

(10) Patent No.: US 11,541,090 B2
(45) Date of Patent: Jan. 3, 2023

(54) COMPOSITION FOR ELIMINATING HOUSEHOLD PET ALLERGENS

(71) Applicant: NINGBO RHYSUAIR BIOTECHNOLOGY CO.,LTD., Ningbo (CN)

(72) Inventor: Jian Zhou, Ningbo (CN)

(73) Assignee: Ningbo Rhysuair Biotechnology Co., Ltd., Ningbo (CN)

( * ) Notice: Subject to any disclaimer, the term of this patent is extended or adjusted under 35 U.S.C. 154(b) by 57 days.

(21) Appl. No.: 17/338,232

(22) Filed: Jun. 3, 2021

(65) Prior Publication Data

US 2022/0378860 A1     Dec. 1, 2022

(30) Foreign Application Priority Data

May 26, 2021   (CN) .......................... 202110576495.2

(51) Int. Cl.
    *A61K 36/185*      (2006.01)

(52) U.S. Cl.
CPC ........ *A61K 36/185* (2013.01); *A61K 2236/13* (2013.01); *A61K 2236/15* (2013.01); *A61K 2236/53* (2013.01)

(58) Field of Classification Search
None
See application file for complete search history.

(56) References Cited

U.S. PATENT DOCUMENTS

| | | | |
|---|---|---|---|
| 6,395,394 B1 | 5/2002 | Willemsen |
| 6,852,244 B2 | 2/2005 | Egawa et al. |
| 6,989,035 B2 | 1/2006 | Scheper et al. |
| 7,008,457 B2 | 3/2006 | Sivik et al. |
| 7,309,726 B2 | 12/2007 | Wakita et al. |
| 7,381,231 B2 | 6/2008 | Smith et al. |
| 10,640,739 B2 | 5/2020 | Shan et al. |
| 10,815,149 B2 | 10/2020 | Dubey et al. |
| 2003/0088923 A1 | 5/2003 | Sivik et al. |
| 2005/0054702 A1 | 3/2005 | Dunn et al. |
| 2007/0209731 A1 | 9/2007 | Chang |
| 2010/0209530 A1 | 8/2010 | Yamada |
| 2013/0273798 A1 | 10/2013 | Yamada |
| 2017/0191010 A1 | 7/2017 | Shan et al. |
| 2018/0179700 A1 | 6/2018 | Wild et al. |
| 2019/0382950 A1 | 12/2019 | Yurchenko |

FOREIGN PATENT DOCUMENTS

DE      102008044700 A1  *  2/2010

\* cited by examiner

*Primary Examiner* — Michael V Meller
(74) *Attorney, Agent, or Firm* — Craft Chu PLLC; Andrew W. Chu

(57) ABSTRACT

The present invention discloses a preparation method and application of anti-cat-and-dog allergen finishing composition solution. The preparation process is as follows: Japanese *Diospyros rhombifolia* Hemsl and Canangaodorata petals were washed for 3~5 times, ground and ultrasonically treated to prepare suspension liquid; the suspension liquid was treated by microwave and then centrifuged to obtain light yellow supernate; the light yellow supernate was performed with membrane separation treatment to form a mixed extract of Japanese *Diospyros rhombifolia* Hemsl and Canangaodorata; the obtained mixed extract of Japanese *Diospyros rhombifolia* Hemsl and Canangaodorata was mixed with silver ion compound, *Eucalyptus* oil, fatty alcohol polyoxyethylene ether, sodium dodecyl benzene sulfonate, sodium laurate, sodium stearate, citric acid, serine protease, pectinase, cellulase, xylanase, beta-glucanase, glycerol, cetyldimethyl benzyl ammonium chloride, chitosan, pigment, plant essence, preservative and deionized water evenly, according to a certain mass share ratio; ultrasonically vibrating the mixture at a certain temperature for a certain time, and cooling the mixture to room temperature to obtain the anti-cat-and-dog allergen finishing composition solution. The preparation method of the composition is simple, and can be used for daily spraying and wiping, and can also be used in the washing or drying process of clothes.

5 Claims, 2 Drawing Sheets

COMPOSITION FOR ELIMINATING HOUSEHOLD PET ALLERGENS

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to the technical field of a composition for eliminating household pet allergens, and specifically to a preparation method and application of the composition for de-activating the active ingredients in household pet allergens.

2. Description of Related Art Including Information Disclosed Under 37 CFR 1.97 and 37 CFR 1.98

In recent years, raising pets has become a popular trend for modern parents. According to annual consumer reports, the demand for household pets has increase, and pet products are becoming more and more abundant. In the pet products market, the demand for cleaning and caring is the largest. However, when raising pets, if pet allergens, such as dandruff, sebaceous skin secretion, saliva, urine and bird feather dust, are inhaled, then up to 10% of the general population and 40% of allergic individuals will have allergic or asthmatic reactions. In particular, cat allergens, which are small in size and very light in weight, circulate in the airflow of the whole house, and can float in the air for several hours and enter anything they contact, such as carpets, bedding, upholstered furniture, coarse textured fabrics, walls, heating pipes, and air conditioners. Therefore, people with household pets have a use for a cleaning or treatment product to eliminate or disable household pet allergens with a simple preparation method and without side effects on pets and human beings.

BRIEF SUMMARY OF THE INVENTION

The present invention includes the mixed extract of Japanese *Diospyros rhombifolia* Hemsl and *Cananga odorata*, silver ion compounds and natural substances such as *eucalyptus* oil, as the main components. The components are processed by advanced technical means, such as ultrasound treatment, microwave treatment, membrane treatment and the like, so as to form a composition for eliminating household pet allergens or at least disabling active components in household pet allergens.

The present invention provides a method for a composition solution to eliminate household pet allergens, comprising the following steps:

(1) washing Japanese *Diospyros rhombifolia* Hemsl petals and *Cananga odorata* petals 3~5 times, grinding the petals and ultrasonically treating the petals so as to prepare a suspension liquid;

(2) microwave treating and centrifuging the suspension liquid so as to obtain a light yellow supernate;

(3) performing a membrane separation treatment on the light yellow supernate so as to form an extract;

(4) mixing the extract, nanometer Nagasaki shell powder, silver ion compound, *Eucalyptus* oil, fatty alcohol polyoxyethylene ether, sodium dodecyl benzene sulfonate, sodium laurate, sodium stearate, citric acid, serine protease, pectinase, cellulase, xylanase, beta-glucanase, glycerol, cetyldimethyl benzyl ammonium chloride, chitosan, pigment, plant essence, preservative and deionized water evenly, according to a certain mass share ratio, so as to form a mixture, and ultrasonically vibrating the mixture at a certain temperature for a certain time, and cooling the mixture to room temperature so as to obtain a composition for eliminating household pet allergens.

The preparation method of the composition for eliminating household pet allergens is characterized in that: the ultrasonic treatment conditions in the step (1) are as follows: the ultrasonic temperature is 30-80 deg. C. and the ultrasonic time is 15-60 min. Preferably, the ultrasonic temperature is 40~60 deg. C. and the ultrasonic time is 30-60 min.

The preparation method of the composition for eliminating household pet allergens is characterized in that: the microwave treatment conditions in the step (2) are as follows: the microwave output power is 300~800 W, the time is 20-45 min, and the temperature is 30-80 deg. C. Preferably, the microwave output power is 400~600 W, the time is 25~45 min, and the temperature is 60-80 deg. C.

The preparation method of the composition for eliminating household pet allergens is characterized in that: the centrifugal treatment conditions in the step (2) are as follows: the rotating speed is 300-1500 r/min and the centrifugal time is 5-30 min. Preferably, the rotating speed is 800~1500 r/min and the centrifugal time is 5~15 min.

The preparation method of the composition for eliminating household pet allergens is characterized in that: the conditions of membrane separation treatment in the step (3) are as follows: the ultrafiltration membrane operating pressure difference is 0.1~5 MPa, nanofiltration membrane operating pressure difference is 0.1~5 MPa, membrane surface flow rate is 0.5-5 m/s and the temperature is 35~55 deg. C. Preferably, the ultrafiltration membrane operating pressure difference is 0.1~3 MPa, nanofiltration membrane operating pressure difference is 0.1~3 MPa, membrane surface flow rate is 0.5~2.5 m/s, the temperature is 35~45 deg. C.

The preparation method of the composition for eliminating household pet allergens is characterized in that: the certain mass share ratio in the step (4) is 2-5 shares of mixed extract of Japanese *Diospyros rhombifolia* Hemsl and *Cananga odorata*, 2-5 shares of silver ion compound, 5-30 shares of *eucalyptus* oil, 5-20 shares of fatty alcohol polyoxyethylene ether, 5-20 shares of sodium dodecyl benzene sulfonate, 0.05-1 share of sodium laurate, 0.05-1 share of sodium stearate, 2-5 shares of citric acid, 0.5-1 share of serine protease, 0.5-1 share of pectinase, 0.5-1 share of cellulose, 0.5 to 1 share of xylanase, 0.5 to 1 share of beta-glucanase, 20 to 40 shares of glycerol, 0.05-1 share of cetyldimethyl benzyl ammonium chloride, 5-10 shares of chitosan, 0.1-0.5 share of pigment, 2-3 shares of plant essence, 0.2-1 share of preservative and 20-50 shares of deionized water; preferably, 2-3 shares of Japanese *Diospyros rhombifolia* Hemsl, 2-3 shares of Nagasaki shell powder, 2-3 shares of silver ion compound, 5-20 shares of *Eucalyptus* oil, 5-10 shares of fatty alcohol polyoxyethylene ether, 5-15 shares of sodium dodecyl benzene sulfonate, 0.05-0.5 share of sodium laurate, 0.05-0.5 share of sodium stearate, 4-5 shares of citric acid, 0.5 to 1 share of serine protease, 0.5 to 1 share of pectinase, 0.5 to 1 share of cellulase, 0.5 to 1 share of xylanase, 0.5 to 1 share of beta-glucanase, 25-40 shares of glycerol, 0.5 to 1 share of cetyldimethyl benzyl ammonium chloride, 8-10 shares of chitosan, 0.1-0.5 share of pigment, 2-10 shares of plant essence, 0.2 to 1 share of preservative and 20-40 shares of deionized water.

The preparation method of the composition for eliminating household pet allergens is characterized in that: in the step (4), the certain temperature is 45-65 deg. C., and the certain time is 2-10 hours. Preferably, the certain temperature is 55~65 deg C., and the certain time is 6-8 hours.

The present invention takes the mixed extract of Japanese *Diospyros rhombifolia* Hemsl and *Cananga odorata*, *eucalyptus* oil, silver ion compounds and other substances as the main components, applies advanced technical means, such as ultrasound treatment, microwave treatment, membrane treatment and the like, and uses antibacterial components, such as choline, rutin, tannin and the like extracted from Japanese *Diospyros rhombifolia* Hemsl, *Cananga odorata* essential oil extracted from *Cananga odorata*, *eucalyptus* oil and silver ion to produce a reaction with protein of major allergens in cats and dogs, so as to achieve the efficacy of eliminating or disabling household pet allergens. The composition can be used for daily spraying and wiping, and can also be used in the washing or drying process of clothes.

DETAILED DESCRIPTION OF THE INVENTION

Figure 1:
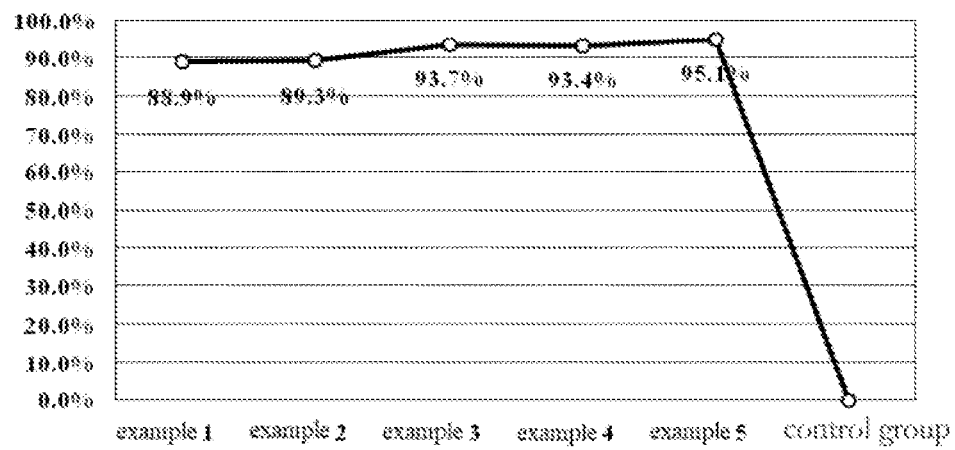
FIG. 1 is a graph illustration of an antiallergic effect of an embodiment of the composition with different mass ratios on cat allergen Fel d1 in Embodiments 1-5 of the present invention.

The method of the present invention will be described in detail with specific embodiments, which are implemented on the premise of the technical solutions of the present invention, but the protection scope of the present invention is not limited to the following embodiments.

Embodiment 1

Japanese *Diospyros rhombifolia* Hemsl and *Cananga odorata* petals were washed for 3~5 times, ground, and ultrasonically treated under 40 deg C. for 30 min to suspension liquid. The suspension liquid was treated by microwave under 60 deg C. for 25 min wherein microwave output power is set to 400 W and then was centrifuged under 1500 r/min for 5 min, to obtain the light yellow supernate. The light yellow supernate was performed with membrane separation treatment under 55 deg C., wherein the ultrafiltration membrane operating pressure difference is 0.5 MPa, the nanofiltration membrane operating pressure difference is 0.5 MPa, and the membrane surface flow rate is 0.5 m/s, to form a mixed extract of Japanese *Diospyros rhombifolia* Hemsl and *Cananga odorata*. Mixing is performed according to the mass share ratio of 2 shares of the mixed extract of Japanese *Diospyros rhombifolia* Hemsl and *Cananga odorata*, 2 shares of silver ion compound, 5 shares of *eucalyptus* oil, 15 shares of fatty alcohol polyoxyethylene ether, 15 shares of sodium dodecyl benzene sulfonate, 1 share of sodium laurate, 1 share of sodium stearate, 5 shares of citric acid, 1 share of serine protease, 1 share of cellulase, 1 share of pectinase, 1 share of cellulose, 1 share of xylanase, 1 share of beta-glucanase, 35 shares of glycerol, 1 share of cetyldimethyl benzyl ammonium chloride, 8 shares of chitosan, 0.1 share of pigment, 2 shares of plant essence, 0.2 share of preservative and 35 shares of deionized water. The mixture is ultrasonically vibrated at 65 deg C. for 6 hours, and is cooled to room temperature to obtain the composition for eliminating or disabling household pet allergens.

Embodiment 2

Japanese *Diospyros rhombifolia* Hemsl and *Cananga odorata* petals were washed for 3~5 times, ground, and ultrasonically treated under 40 deg C. for 30 min to suspension liquid. The suspension liquid was treated by microwave under 60 deg C. for 25 min wherein microwave output power is set to 400 W and then was centrifuged under 1500 r/min for 5 min, to obtain the light yellow supernate. The light yellow supernate was performed with membrane separation treatment under 55 deg C., wherein the ultrafiltration membrane operating pressure difference is 0.5 MPa, the nanofiltration membrane operating pressure difference is 0.5 MPa, and the membrane surface flow rate is 0.5 m/s, to form a mixed extract of Japanese *Diospyros rhombifolia* Hemsl and *Cananga odorata*. Mixing is performed according to the mass share ratio of 3 shares of the mixed extract of Japanese *Diospyros rhombifolia* Hemsl and *Cananga odorata*, 2 shares of silver ion compound, 5 shares of *eucalyptus* oil, 15 shares of fatty alcohol polyoxyethylene ether, 15 shares of sodium dodecyl benzene sulfonate, 1 share of sodium laurate, 1 share of sodium stearate, 5 shares of citric acid, 1 share of serine protease, 1 share of cellulase, 1 share of pectinase, 1 share of cellulose, 1 share of xylanase, 1 share of beta-glucanase, 35 shares of glycerol, 1 share of cetyldimethyl benzyl ammonium chloride, 8 shares of chitosan, 0.1 share of pigment, 2 shares of plant essence, 0.2 share of preservative and 35 shares of deionized water. The mixture is ultrasonically vibrated at 65 deg C. for 6 hours, and is cooled to room temperature to obtain the composition for eliminating or disabling household pet allergens.

Embodiment 3

Japanese *Diospyros rhombifolia* Hemsl and *Cananga odorata* petals were washed for 3~5 times, ground, and ultrasonically treated under 40 deg C. for 30 min to suspension liquid. The suspension liquid was treated by microwave under 60 deg C. for 25 min wherein microwave output power is set to 400 W and then was centrifuged under 1500 r/min for 5 min, to obtain the light yellow supernate. The light yellow supernate was performed with membrane separation treatment under 55 deg C., wherein the ultrafiltration membrane operating pressure difference is 0.5 MPa, the nanofiltration membrane operating pressure difference is 0.5 MPa, and the membrane surface flow rate is 0.5 m/s, to form a mixed extract of Japanese *Diospyros rhombifolia* Hemsl and *Cananga odorata*. Mixing is performed according to the mass share ratio of 5 shares of the mixed extract of Japanese *Diospyros rhombifolia* Hemsl and *Cananga odorata*, 2 shares of silver ion compound, 5 shares of *eucalyptus* oil, 15 shares of fatty alcohol polyoxyethylene ether, 15 shares of sodium dodecyl benzene sulfonate, 1 share of sodium laurate, 1 share of sodium stearate, 5 shares of citric acid, 1 share of serine protease, 1 share of cellulase, 1 share of pectinase, 1 share of cellulose, 1 share of xylanase, 1 share of beta-glucanase, 35 shares of glycerol, 1 share of cetyldimethyl benzyl ammonium chloride, 8 shares of chitosan, 0.1 share of pigment, 2 shares of plant essence, 0.2 share of preservative and 35 shares of deionized water. The mixture is ultrasonically vibrated at 65 deg C. for 6 hours, and is cooled to room temperature to obtain the composition for eliminating or disabling household pet allergens.

Embodiment 4

Japanese *Diospyros rhombifolia* Hemsl and *Cananga odorata* petals were washed for 3~5 times, ground, and ultrasonically treated under 40 deg C. for 30 min to suspension liquid. The suspension liquid was treated by microwave under 60 deg C. for 25 min wherein microwave output power is set to 400 W and then was centrifuged under 1500 r/min for 5 min, to obtain the light yellow supernate. The light yellow supernate was performed with membrane separation treatment under 55 deg C., wherein the ultrafiltration membrane operating pressure difference is 0.5 MPa, the nanofiltration membrane operating pressure difference is 0.5 MPa, and the membrane surface flow rate is 0.5 m/s, to form a mixed extract of Japanese *Diospyros rhombifolia* Hemsl and *Cananga odorata*. Mixing is performed according to the mass share ratio of 2 shares of the mixed extract of Japanese *Diospyros rhombifolia* Hemsl and *Cananga odorata*, 3 shares of silver ion compound, 5 shares of *eucalyptus* oil, 15 shares of fatty alcohol polyoxyethylene ether, 15 shares of sodium dodecyl benzene sulfonate, 1 share of sodium laurate, 1 share of sodium stearate, 5 shares of citric acid, 1 share of serine protease, 1 share of cellulase, 1 share of pectinase, 1 share of cellulose, 1 share of xylanase, 1 share of beta-glucanase, 35 shares of glycerol, 1 share of cetyldimethyl benzyl ammonium chloride, 8 shares of chitosan, 0.1 share of pigment, 2 shares of plant essence, 0.2 share of preservative and 35 shares of deionized water. The mixture is ultrasonically vibrated at 65 deg C. for 6 hours, and is cooled to room temperature to obtain the composition for eliminating or disabling household pet allergens.

Embodiment 5

Japanese *Diospyros rhombifolia* Hemsl and *Cananga odorata* petals were washed for 3~5 times, ground, and ultrasonically treated under 40 deg C. for 30 min to suspension liquid. The suspension liquid was treated by microwave under 60 deg C. for 25 min wherein microwave output power is set to 400 W and then was centrifuged under 1500 r/min for 5 min, to obtain the light yellow supernate. The light yellow supernate was performed with membrane separation treatment under 55 deg C., wherein the ultrafiltration membrane operating pressure difference is 0.5 MPa, the nanofiltration membrane operating pressure difference is 0.5 MPa, and the membrane surface flow rate is 0.5 m/s, to form a mixed extract of Japanese *Diospyros rhombifolia* Hemsl and *Cananga odorata*. Mixing is performed according to the mass share ratio of 5 shares of the mixed extract of Japanese *Diospyros rhombifolia* Hemsl and *Cananga odorata*, 5 shares of Nagasaki shell powder, 5 shares of silver ion compound, 5 shares of *eucalyptus* oil, 15 shares of fatty alcohol polyoxyethylene ether, 15 shares of sodium dodecyl benzene sulfonate, 1 share of sodium laurate, 1 share of sodium stearate, 5 shares of citric acid, 1 share of serine protease, 1 share of cellulase, 1 share of pectinase, 1 share of cellulose, 1 share of xylanase, 1 share of beta-glucanase, 35 shares of glycerol, 1 share of cetyldimethyl benzyl ammonium chloride, 8 shares of chitosan, 0.1 share of pigment, 2 shares of plant essence, 0.2 share of preservative and 35 shares of deionized water. The mixture is ultrasonically vibrated at 65 deg C. for 6 hours, and is cooled to room temperature to obtain the composition for eliminating or disabling household pet allergens Performance Test The main allergen of cats is Feld1, which is a glycoprotein secreted by sebaceous glands that mainly exists in its dander, saliva and urine. The main allergen of dogs is Canf1, which mainly exists in its dander, saliva, urine and serum.

Test I

Two pieces of cotton cloth with the same texture and size, numbered a and b, were respectively placed in cat allergen extract Fel d1 and dog allergen extract Can f1 with the concentration of 5000 ng/mL, and soaked for 24 hours at room temperature. The above two pieces of cotton cloth are respectively divided into six equal parts, numbered as a1, a2, a3, a4, a5, a6, b1, b2, b3, b4, b5 and b6.

Cotton cloth parts numbered as a1, a2, a3, a4, a5 was soaked in the composition of the present invention prepared in Embodiments 1-5 for 45 min. Cotton cloth part numbered as a6 is soaked in purified water for 45 min. MARIA™ (Multiplex Array for indoor Allergens) method is used to detect antiallergic effects of the composition of the present invention with different mass ratios on cat allergen Fel d1, and the detection results are shown in FIG. 1.

Figure 2:
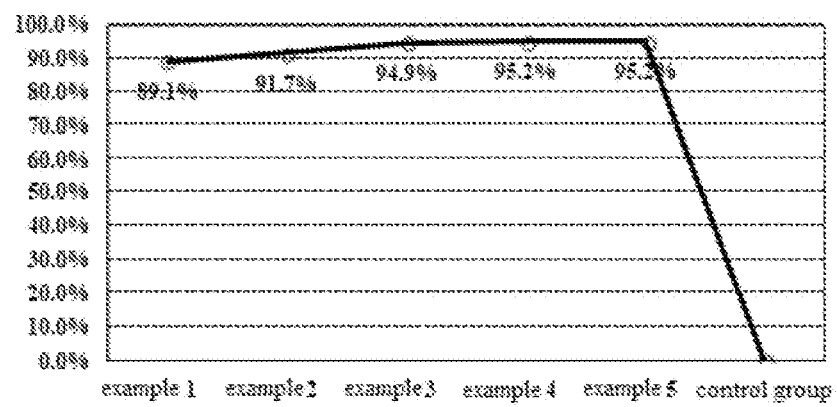
FIG. 2 is a graph illustration of an antiallergic effect of an embodiment of the composition with different mass ratios on dog allergen Can f1 in Embodiments 1-5 of the present invention.

Cotton cloth parts numbered as b1, b2, b3, b4, b5 was soaked in the composition of the present invention prepared in Embodiments 1-5 for 45 min. Cotton cloth part numbered as b6 is soaked in purified water for 45 min. MARIA™ technology is used to detect the antiallergic effect of prepared finishing composition solutions with different mass ratios on dog allergen Can f1, and the detection result is shown in FIG. 2.

Test II

Figure 3:
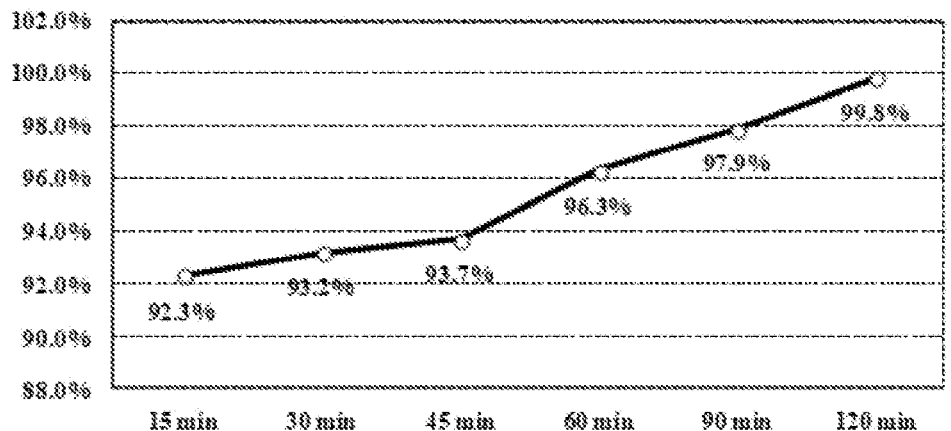
FIG. 3 is a graph illustration of an antiallergic effect of the composition on cat allergen Fel d1 under different reaction time in Embodiment 3 of the present invention.

Cotton cloths that have been treated the same way as a1, a2, a3, a4, a5, a6, are soaked in the composition of the present invention prepared in Embodiment 3 for 15 min, 30 min, 45 min, 60 min, 90 min and 120 min. The MARIA™ (Multiplex Array for indoor Allergens) method is used to detect the anti-allergic effect of different reaction time on cat allergen Fel d1, and the detection result is shown in FIG. 3.

Figure 4:
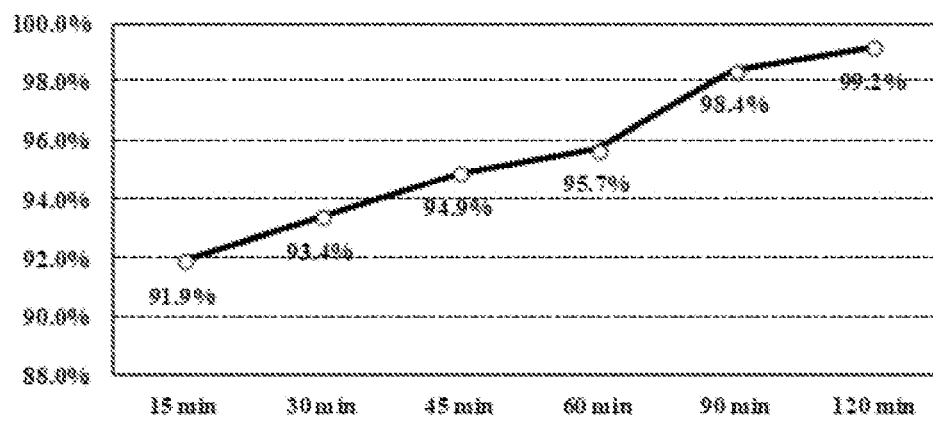
FIG. 4 is a graph illustration of an antiallergic effect chart of the composition on dog allergen Can f1 under different reaction time in Embodiment 3 of the present invention.

Cotton cloths that have been treated the same way as b1, b2, b3, b4, b5, b6, are soaked in the composition of the present invention prepared in Embodiment 3 for 15 min, 30 min, 45 min, 60 min, 90 min and 120 min. The MARIA™ (Multiplex Array for indoor Allergens) method is used to detect the anti-allergic effect of different reaction time on dog allergen Can f1, and the detection result is shown in FIG. 4.

I claim:

1. A method for eliminating household pet allergens, consisting essentially of the following steps:
   (a) washing Japanese *Diospyros rhombifolia* Hemsl and *Cananga odorata* petals 3~5 times,
   (b) grinding the petals,
   (c) ultrasonically treating the petals so as to prepare a suspension liquid,
   (d) treating the suspension liquid with microwaves,
   (e) centrifuging to obtain a light yellow supernatant,
   (f) filtering the light yellow supernatant with a membrane separation treatment to form a mixed extract of Japanese *Diospyros rhombifolia* Hemsl and *Cananga odorata*,
   (g) mixing the mixed extract with *Eucalyptus* oil, fatty alcohol polyoxyethylene ether, sodium dodecyl benzene sulfonate, sodium laurate, sodium stearate, citric acid, serine protease, pectinase, cellulase, xylanase, beta-glucanase, glycerol, cetyldimethyl benzyl ammonium chloride, chitosan, and deionized water to form a mixture, and
   (h) ultrasonically vibrating the mixture at 45° C.-65° C. for 2-10 hours, and then cooling the mixture to room temperature to obtain the anti-cat-and-dog allergen finishing composition solution to be administered to an area for eliminating household pet allergens.

2. The method for eliminating household pet allergens, according to claim 1, wherein, in the step of ultrasonically treating the petals of step (c), an ultrasonic temperature is 30° C.-80° C. for 15-60 min.

3. The method for eliminating household pet allergens, according to claim 1, wherein, in the step of treating the suspension liquid with microwaves of step (d), a microwave output power is 300~800 W for 20-45 min at 30° C.-80° C.

4. The method for eliminating household pet allergens, according to claim 1, wherein, in the step of centrifuging of step (e), a rotating speed is 300-1500 r/min for 5~30 min.

5. The method for eliminating household pet allergens, according to claim 1, wherein, in the step of filtering the light yellow supernatant of step (f), an ultrafiltration membrane operating pressure difference is 0.1~5 MPa, a nanofiltration membrane operating pressure difference being 0.1~5 MPa, and a membrane surface flow rate being 0.5~5 m/s at 35° C.~55° C.

* * * * *